United States Patent
Thenuwara et al.

(10) Patent No.: US 10,016,589 B2
(45) Date of Patent: *Jul. 10, 2018

(54) MID-SCALAR ELECTRODE ARRAY

(71) Applicant: Advanced Bionics AG, Staefa (CH)

(72) Inventors: Chuladatta Thenuwara, Valencia, CA (US); Rosa Gallegos, Sylmar, CA (US); Lidia Vasquez, Palmdale, CA (US); Mark B. Downing, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/204,594

(22) Filed: Jul. 7, 2016

(65) Prior Publication Data

US 2016/0317801 A1  Nov. 3, 2016

Related U.S. Application Data

(63) Continuation of application No. 14/116,089, filed as application No. PCT/US2011/036051 on May 11, 2011, now Pat. No. 9,415,207.

(51) Int. Cl.
  *A61N 1/05* (2006.01)
  *A61N 1/36* (2006.01)

(52) U.S. Cl.
  CPC ....... *A61N 1/0541* (2013.01); *A61N 1/36036* (2017.08); *Y10T 29/49224* (2015.01)

(58) Field of Classification Search
  CPC .......................... A61N 1/0541; A61N 1/36032
  See application file for complete search history.

(56) References Cited

U.S. PATENT DOCUMENTS

| | | | |
|---|---|---|---|
| 4,832,051 A | 5/1989 | Jarvik et al. | |
| 5,545,219 A | 8/1996 | Kuzma | |
| 6,421,569 B1 | 7/2002 | Wollstonecraft et al. | |
| 7,319,906 B2 | 1/2008 | Kuzma et al. | |
| 7,774,071 B2 | 8/2010 | Schuller | |
| 8,180,459 B2 | 5/2012 | Dadd et al. | |
| 8,244,366 B2 | 8/2012 | Chang et al. | |
| 8,457,764 B2 | 11/2013 | Ramachandran et al. | |
| 2004/0116995 A1 | 6/2004 | Dadd | |
| 2004/0147992 A1 | 7/2004 | Bluger | |
| 2004/0220651 A1 | 11/2004 | Kuzma et al. | |
| 2004/0238819 A1 | 12/2004 | Maghribi | |
| 2004/0243204 A1 | 12/2004 | Maghribi | |
| 2005/0267558 A1 | 12/2005 | Frijns et al. | |
| 2006/0085055 A1 | 4/2006 | Dadd et al. | |

(Continued)

FOREIGN PATENT DOCUMENTS

| | | |
|---|---|---|
| WO | 2000071063 | 11/2000 |
| WO | 2007090655 | 8/2007 |

(Continued)

*Primary Examiner* — Allen Porter, Jr.
(74) *Attorney, Agent, or Firm* — Gregory Rosenthal; Mary Elizabeth Bush

(57) ABSTRACT

In one example, a cochlear lead includes a flexible body, an array of electrodes in the flexible body, and a plurality of wires passing along the array of electrodes. The plurality of wires includes a flexural geometry between each pair of adjacent electrodes and a substantially straight geometry over the electrodes. A method for forming an electrode array with a reduced apical cross section is also provided.

19 Claims, 11 Drawing Sheets

Section A-A

(56) References Cited

U.S. PATENT DOCUMENTS

| | | |
|---|---|---|
| 2006/0122664 A1* | 6/2006 | Sacha .................. A61N 1/0541 607/57 |
| 2006/0206185 A1 | 9/2006 | Schuller |
| 2007/0123963 A1 | 5/2007 | Krulevitch |
| 2008/0082141 A1 | 4/2008 | Risi |
| 2008/0234793 A1 | 9/2008 | Gibson |
| 2010/0204768 A1 | 8/2010 | Jolly et al. |
| 2011/0034969 A1 | 2/2011 | Capcelea |
| 2011/0180305 A1 | 7/2011 | Johnson |
| 2012/0004715 A1 | 1/2012 | Ramachandran et al. |
| 2012/0296405 A1 | 11/2012 | Thenuwara |

FOREIGN PATENT DOCUMENTS

| | | |
|---|---|---|
| WO | 2009062114 | 5/2009 |
| WO | 2009154904 | 12/2009 |
| WO | 2010005627 | 1/2010 |
| WO | 2012003295 | 1/2012 |

\* cited by examiner

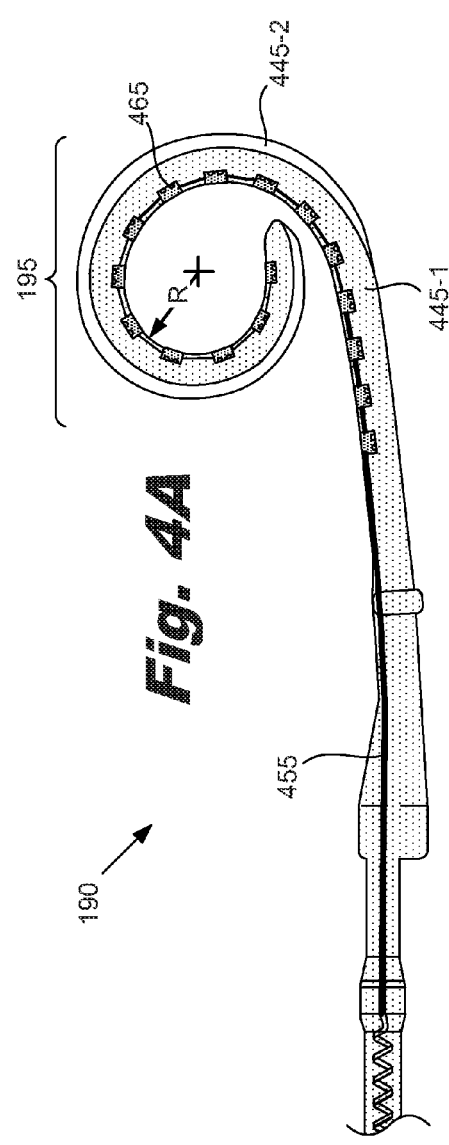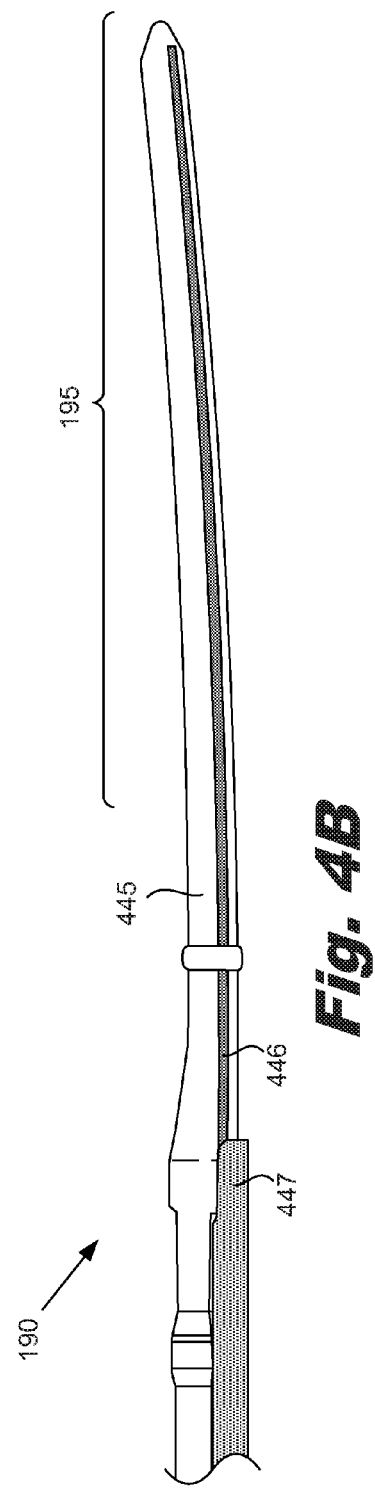

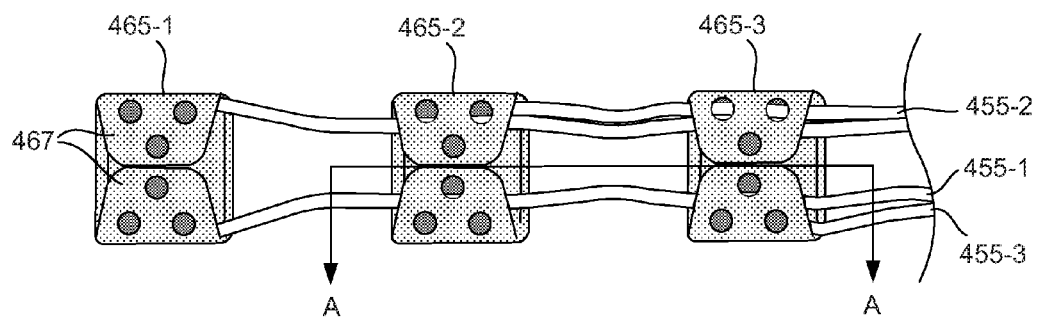
Fig. 5A
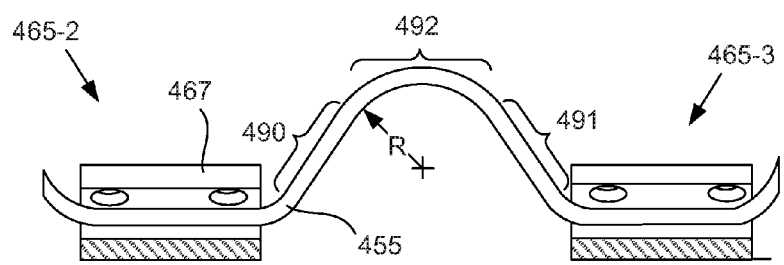
Fig. 5B Section A-A
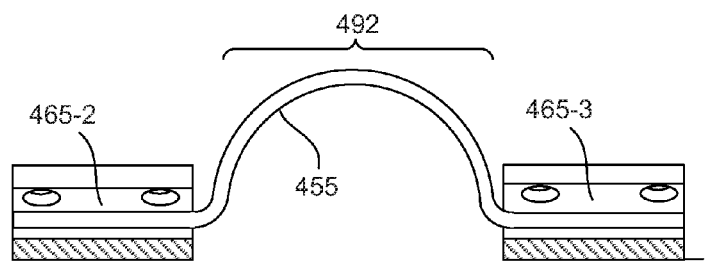
Fig. 5C Section A-A
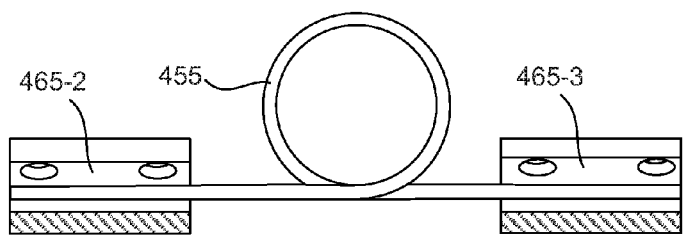
Fig. 5D Section A-A

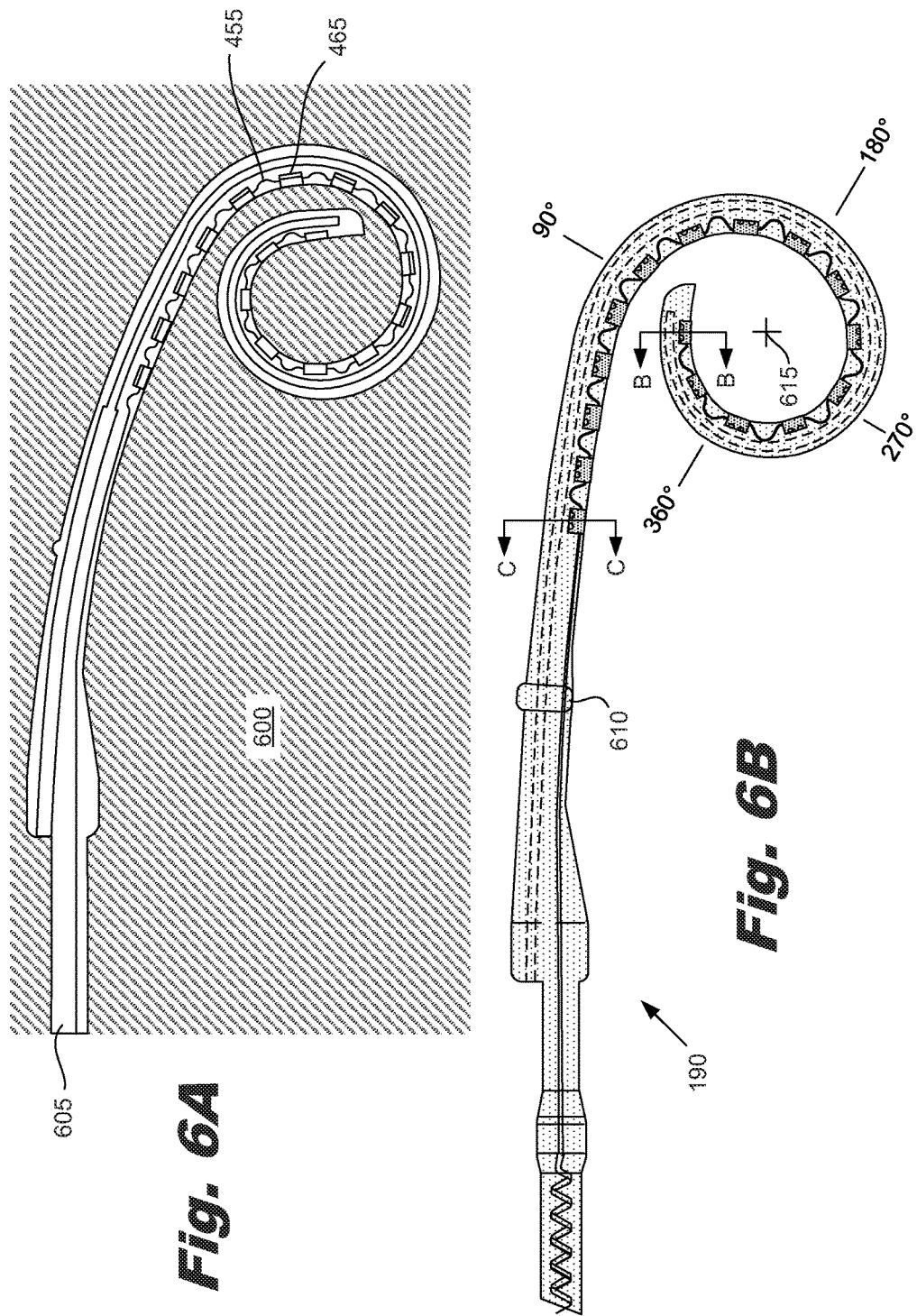

MID-SCALAR ELECTRODE ARRAY

This application is a continuation of U.S. application Ser. No. 14/116,089, now U.S. Pat. No. 9,415,207, which has a 35 U.S.C. § 371(c) date of Nov. 6, 2013, which is the U.S. National Stage of PCT App. Ser. No. PCT/US2011/036051, filed May 11, 2011. The content of each application is incorporated herein by reference in its entirety.

BACKGROUND

In human hearing, hair cells in the cochlea respond to sound waves and produce corresponding auditory nerve impulses. These nerve impulses are then conducted to the brain and perceived as sound.

Hearing loss, which may be due to many different causes, is generally of two types: conductive and sensorineural. Conductive hearing loss typically occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also treatable by surgical procedures.

Many people who are profoundly deaf, however, have sensorineural hearing loss. This type of hearing loss can arise from the absence or the destruction of the hair cells in the cochlea which then no longer transduce acoustic signals into auditory nerve impulses. Individuals with sensorineural hearing loss may be unable to derive significant benefit from conventional hearing aid systems alone, no matter how loud the acoustic stimulus is. This is because the natural mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems, or cochlear prostheses, have been developed that can bypass the hair cells located in the cochlea by presenting electrical stimulation directly to the auditory nerve fibers. This leads to the perception of sound in the brain and provides at least partial restoration of hearing function. Most of these cochlear prosthesis systems treat sensorineural deficit by stimulating the ganglion cells in the cochlea directly using an implanted electrode or lead that has an electrode array. Thus, a cochlear prosthesis operates by directly stimulating the auditory nerve cells, bypassing the defective cochlear hair cells that normally transduce acoustic energy into electrical activity in the connected auditory nerve cells.

The implantation of the cochlear prosthesis involves the insertion of an electrode array into the cochlea of the patient. The interior structures of the cochlea can be delicate and sensitive to forces generated by the insertion of the electrode array. Minimizing trauma to the cochlea during implantation improves patient outcomes and preserves residual hearing.

BRIEF DESCRIPTION OF THE DRAWINGS

The accompanying drawings illustrate various embodiments of the principles described herein and are a part of the specification. The illustrated embodiments are merely examples and do not limit the scope of the claims.

FIGS. 4A-4D are views of an illustrative electrode array and its positioning within the cochlea, according to one example of principles described herein.

FIGS. 5A-5D are a top view and a cross sectional views of flexural geometries that are formed in signal wires in the electrode array, according to one example of principles described herein.

FIG. 6A is a diagram of an illustrative single shot mold for creating a mid-scalar cochlear lead, according to one example of principles described herein.

FIG. 6B shows an illustrative mid-scalar electrode formed in a single shot mold, according to one example of principles described herein.

Throughout the drawings, identical reference numbers designate similar, but not necessarily identical, elements.

DETAILED DESCRIPTION

Figure 1:
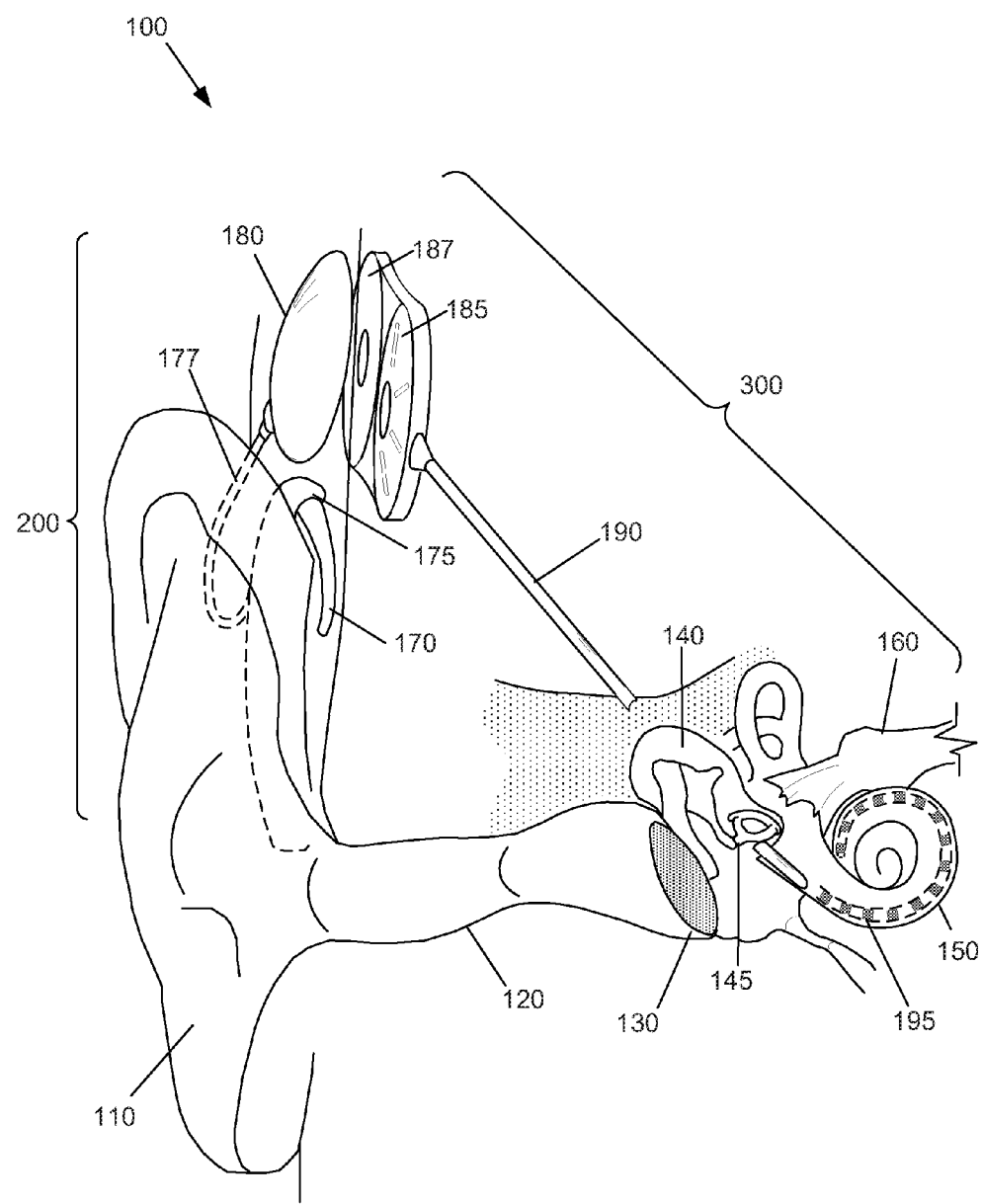
FIG. 1 is an illustrative diagram showing a cochlear implant system in use, according to one example of principles described herein.

As mentioned above, individuals with hearing loss can be assisted by a number of hearing devices, including cochlear implants. The cochlear implant includes a cochlear lead that is surgically implanted into the patient. The distal portion of the lead contains a number of electrodes that electrically stimulate the auditory nerve system. This electrode array is typically constructed out of biocompatible silicone, platinum-iridium wires, and platinum electrodes. To place the lead of a cochlear implant, the distal (or apical) portion of a cochlear lead is pushed through an opening into the cochlea. To reduce trauma and hearing loss, it is desirable that the cochlear lead be inserted into the cochlea with minimal force and reduced contact with the interior structures in the cochlea. In one example, an atraumatic cochlear lead has a thin cross section and mid-scalar placement to prevent or minimize damage to the internal structures of the cochlea. Creating a cochlear lead with a curvature and size that are compatible with the interior geometry of the cochlea can be challenging. In particular, a precurved electrode array with a thin cross section and straight wire may lose the molded curvature due to the resilience of the straight wires. Additional silicone can be added to the electrode array to counteract resilience of the wires. However, the additional silicone makes the electrode array thicker and more difficult to atraumatically insert into the cochlea.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

An electrode array for implantation into the scala tympani typically comprises several separately connected stimulating electrodes, conventionally numbering about 6 to 30, longitudinally disposed on a thin, elongated, flexible carrier. The electrode array is pushed into the scala tympani duct in the cochlea, typically to a depth of about 13-30 mm via a cochleostomy or via a surgical opening made in the round window at the basal end of the duct.

As used in the specification and appended claims, the term "apical" refers to portions or components that are closer to the tip of the cochlear lead. The term "basal" refers to portions or components that are closer to the base of the cochlear lead. For example, an apical electrode is inserted farther into the cochlea than a more basal electrode.

In use, the cochlear electrode array delivers electrical current into the fluids and tissues immediately surrounding the individual electrode contacts to create transient potential gradients that, if sufficiently strong, cause the nearby auditory nerve fibers to generate action potentials. The auditory nerve fibers branch from cell bodies located in the spiral ganglion, which lies in the modiolus, adjacent to the inside wall of the scala tympani. The density of electrical current flowing through volume conductors such as tissues and fluids tends to be highest near the electrode contact that is the source of the current. Consequently, stimulation at one contact site tends to selectively activate those spiral ganglion cells and their auditory nerve fibers that are closest to that electrode.

FIG. 1 is a diagram showing an illustrative cochlear implant system (100) having a cochlear implant (300) with an electrode array (195) that is surgically placed within the patient's cochlea (150). Ordinarily, sound enters the external ear, or pinna, (110) and is directed into the auditory canal (120) where the sound wave vibrates the tympanic membrane (130). The motion of the tympanic membrane (130) is amplified and transmitted through the ossicular chain (140), which includes of three bones in the middle ear. The third bone of the ossicular chain (140), the stapes (145), contacts the outer surface of the cochlea (150) and causes movement of the fluid within the cochlea (150). Cochlear hair cells respond to the fluid-borne vibration in the cochlea (150) and trigger neural electrical signals that are conducted from the cochlea to the auditory cortex by the auditory nerve (160).

As indicated above, the cochlear implant (200, 300) is a surgically implanted electronic device that provides a sense of sound to a person who is profoundly deaf or severely hard of hearing. The cochlear implant (200, 300) operates by direct electrical stimulation of the auditory nerve cells, bypassing the defective cochlear hair cells that normally transduce acoustic energy into electrical energy.

External components (200) of the cochlear implant system can include a Behind-The-Ear (BTE) unit (175), which contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the processor and transmits them to the implanted antenna (187) by electromagnetic transmission.

The components of the cochlear implant (300) include an internal processor (185), an antenna (187), and a cochlear lead (190) having an electrode array (195). The internal processor (185) and antenna (187) are secured beneath the user's skin, typically above and behind the pinna (110). The antenna (187) receives signals and power from the transmitter (180). The internal processor (185) receives these signals and performs one or more operations on the signals to generate modified signals. These modified signals are then sent along a number of signal wires that pass through the cochlear lead (190) and are individually connected to the electrodes in the electrode array (195). The electrode array (195) is implanted within the cochlea (150) and provides electrical stimulation to the auditory nerve (160).

The cochlear implant (300) stimulates different portions of the cochlea (150) according to the frequencies detected by the microphone (170), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

Figure 2:
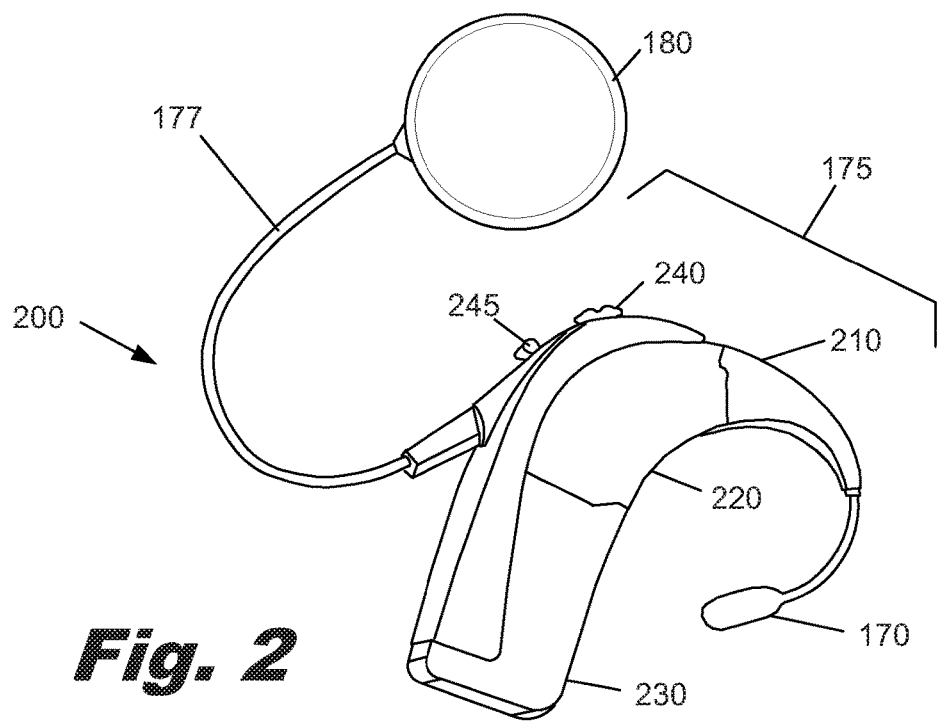
FIG. 2 is a diagram showing external components of an illustrative cochlear implant system, according to one example of principles described herein.

FIG. 2 is an illustrative diagram showing a more detailed view of the external components (200) of a cochlear implant system. External components (200) of the cochlear implant system include a BTE unit (175), which comprises a microphone (170), an ear hook (210), a sound processor (220), and a battery (230), which may be rechargeable. The microphone (170) picks up sound from the environment and converts it into electrical impulses. The sound processor (220) selectively filters and manipulates the electrical impulses and sends the processed electrical signals through a cable (177) to the transmitter (180). A number of controls (240, 245) adjust the operation of the processor (220). These controls may include a volume switch (240) and program selection switch (245). The transmitter (180) receives the processed electrical signals from the processor (220) and transmits these electrical signals and power from the battery (230) to the cochlear implant (300) by electromagnetic transmission.

Figure 3:
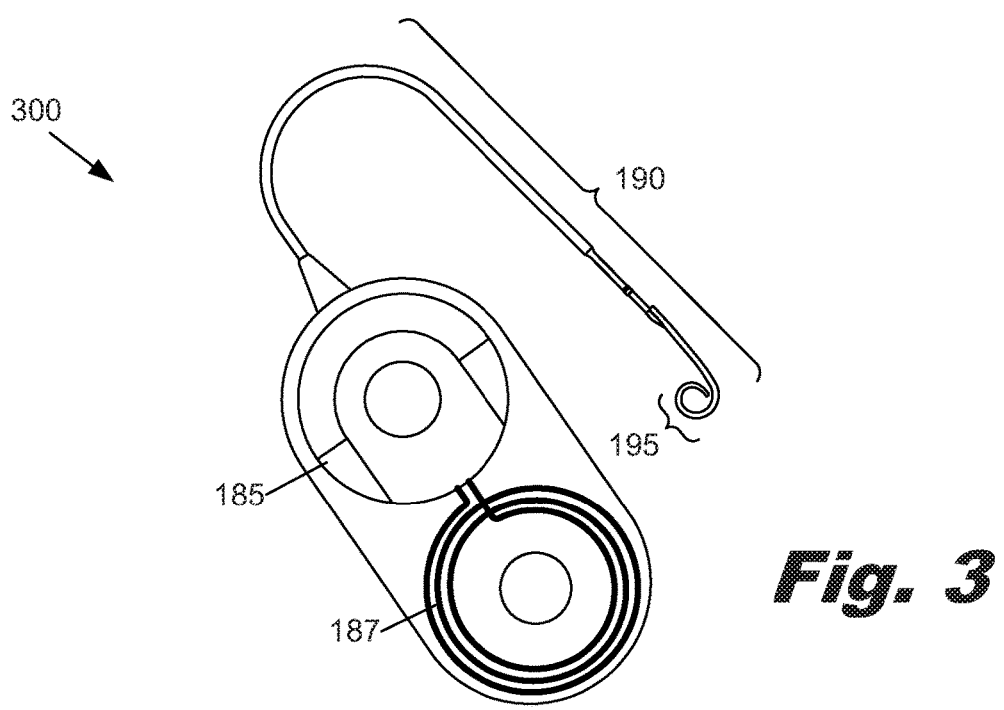
FIG. 3 is a diagram showing the internal components of an illustrative cochlear implant system, according to one example of principles described herein.

FIG. 3 is an illustrative diagram showing one embodiment of a cochlear implant (300), including an internal processor (185), an antenna (187), and a cochlear lead (190) having an electrode array (195). The cochlear implant (300) is surgically implanted such that the electrode array (195) is internal to the cochlea, as shown in FIG. 1. The internal processor (185) and antenna (187) are secured beneath the user's skin, typically above and behind the pinna (110), with the cochlear lead (190) connecting the internal processor (185) to the electrode array (195) within the cochlea. As discussed above, the antenna (187) receives signals from the transmitter (180) and sends the signals to the internal processor (185). The internal processor (185) modifies the signals and passes them along the appropriate wires to activate one or more of the electrodes within the electrode array (195). This provides the user with sensory input that is a representation of external sound waves sensed by the microphone (170).

FIG. 4A is a diagram of an illustrative cochlear lead (190) formed using a two-step molding process. In this example, the cochlear lead (190) includes an electrode array (195) made up of electrodes (465), wires (455) that electrically connect each of the electrodes (465) to the internal processor (185, FIG. 3), and a flexible body (445) that encapsulates the wires (455) and electrodes (465). As discussed above, the cochlea has a spiral shape. In this example, the electrode array (195) has a tight curvature that matches interior geometry of the cochlea. For example, the apical portion of the electrode array (195) may have a radius of curvature R between 1.5 and 1.8 millimeters. The radius of curvature in the electrode array (195) is formed by placing the wires (455) and electrodes (465) in a mold and then filling be mold with a curable encapsulant. For example, the curable encapsulant may be medical grade silicone. The mold has a tighter radius of curvature than the cochlea. When the electrode array (195) is removed from the mold, the electrode array (195) opens up slightly to the relaxed state shown in FIG. 4A. The relaxed state balances the forces produced by the wires and the flexible body. In general, the straight wires tend to open up the electrode array and the silicone tends to resist this opening motion. In the relaxed state, these forces are balanced and the shape of the electrode array approximates the geometry of the interior of the cochlea.

However, the formation of the tight radius of curvature in the mold does not allow enough room for the flexible body (445) to be molded all at once. Instead, a two-step molding process is used. An illustrative two-step molding apparatus and process are described in U.S. Pat. No. 7,319,906 to Janusz Kuzma et al., which is incorporated herein by reference. A first mold forms an initial silicone body (445-1) and a second mold is used to overmold a second silicone body (445-2) over the apical portion of the electrode array (195). Alternatively, the electrode array could be formed into a tighter curvature after the first molding and then manually apply an additional silicone layer. Both of these techniques increase the amount of silicone in the apical portion of the electrode array (195) to resist the straightening forces produced by the wires (455) and maintain the tight curvature of the apical portion of the electrode array (195).

FIG. 4B shows an illustrative step in the insertion of the electrode array (195) into the cochlea. In this step, the electrode array (195) is straightened by inserting a stiffening element (446) into a lumen in the electrode array (195). The tip (447) of an insertion tool is shown supporting the electrode array (195) and stiffening element (446). A cochleostomy is created in the cochlea and the electrode array (195) is inserted into the cochlea through the cochleostomy. To move the electrode array (195) deeper into the cochlea, the electrode (190) is advanced off the stiffening element (446). As it is advanced off the stiffening element (446), the electrode array (195) progressively returns to its relaxed, curved shape. Ideally, the electrode array (195) makes minimal contact with the interior walls of the cochlea and has a relaxed shape that places the electrode array (195) in the desired position within the cochlea. The stiffening element (446) and insertion tool (447) are withdrawn, leaving the cochlear lead (190) in place.

Figure 4C:
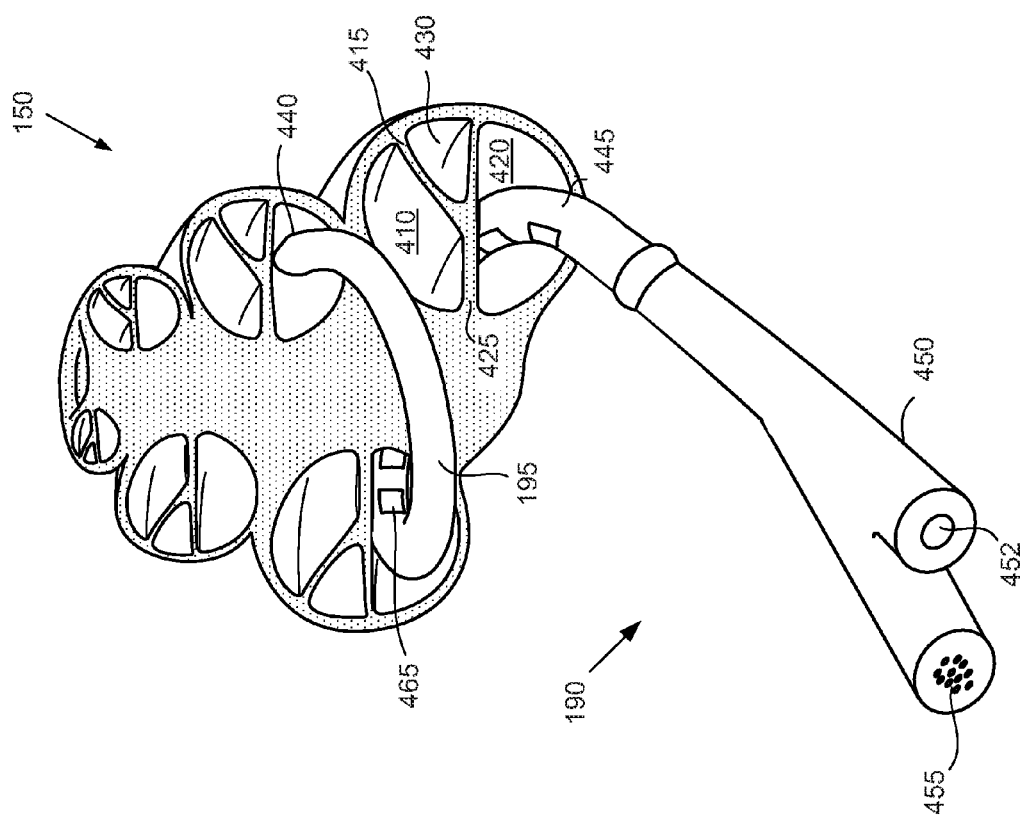

FIG. 4C is a cross sectional view of a cochlea (150) and shows an illustrative electrode array (195) placed within the cochlea (150). As discussed above, the primary structure of the cochlea (150) is a hollow, helically coiled, tubular bone, similar to a nautilus shell. The coiled tube is divided through most of its length into three fluid-filled spaces (scalae). The scala vestibuli (410) is partitioned from the scala media (430) by Reissner's membrane (415) and lies superior to it. The scala tympani (420) is partitioned from the scala media (430) by the basilar membrane (425) and lies inferior to it. A typical human cochlea includes approximately two and a half helical turns of its various constituent channels. The cochlear lead (190) is inserted into one of the scalae, typically the scala tympani (420), to bring the individual electrodes into close proximity with the tonotopically organized nerves.

As can be seen in the cross section, the size of the scala tympani (420) becomes smaller as it spirals upward. As discussed above, the additional silicone layer (445-2. FIG. 4A) added to counteract the resiliency of the straight wires (455, FIG. 4A) thickens the apical portion of the electrode array (195). However, this thicker apical cross section can be undesirable for several reasons. Because the apical portion of the electrode array (195) is inserted farthest into the cochlea (150), the space in the narrowing ducts can become limiting. A thicker apical cross section can lead to more contact and more disruption to structures in the narrow channels. Further, the additional silicone layer stiffens the apical portion of the electrode array. This can lead to higher insertion forces and more forceful contact between the electrode array and interior of the cochlea. Ideally, the apical portion of the electrode array would maintain the desired curvature without the additional silicone layer. This would allow the electrode array to be thin and compliant so as not to damage the cochlear structures.

Figure 4D:
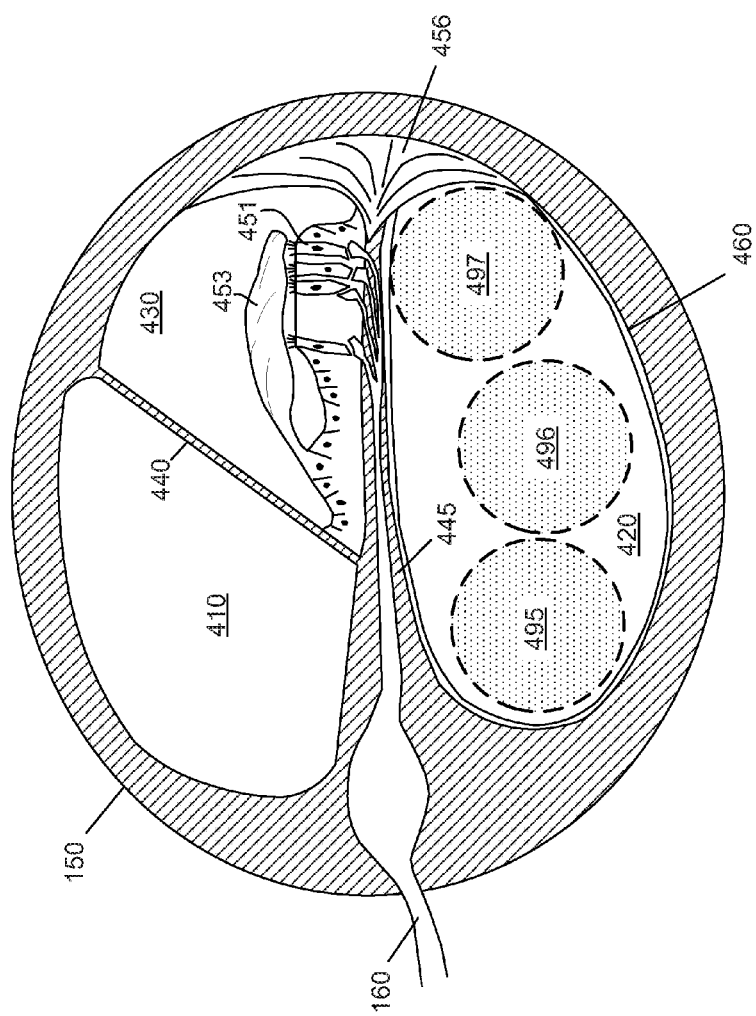

FIG. 4D shows a cross sectional view of a single coil of the cochlea (150). As discussed above, the coiled tube is divided into three fluid-filled spaces (410, 420, 430). The scala vestibuli (410) is partitioned from the scala media (430) by Reissner's membrane (440) and lies superior to it. The scala tympani (420) is partitioned from the scala media (430) by the basilar membrane (445) and lies inferior to it. The bony walls of the cochlea are lined with a membrane, called the periosteum (460), which, in the scala media, is greatly thickened and called the spiral ligament (456). The spiral ligament (456) connects the basilar membrane (445) to the wall of the cochlea.

The cochlea (150) is filled with a fluid that moves in response to the vibrations coming from the middle ear via the stapes (145, FIG. 1). As the fluid moves, a tectorial membrane (453) and thousands of hair cells (451) in a normal, functioning cochlea are set in motion. The hair cells (451) convert that motion to electrical signals that are communicated via neurotransmitters to the auditory nerve (160), and transformed into electrical impulses known as action potentials, which are propagated to structures in the brainstem for further processing. The electrode array is inserted into the scala tympani (420) and the electrical potentials generated by the electrodes stimulate the auditory nerve (160).

The electrode array may be positioned within the scala tympani (420) in one of three general positions that are shown as dashed circles. A medial position (495) locates the electrode array in proximity to the medial wall. A lateral position (497) locates the electrode array in proximity to the lateral wall and adjacent to the spiral ligament (456). Insertion in either of these two positions can involve frictional contact between the electrode array and the walls of the cochlea. This frictional contact may increase the forces used to insert the electrode array into the cochlea.

A third position is the mid-scalar position (496) that locates the electrode array near the center of the scala tympani (420). This position minimizes contact and frictional forces between the electrode array and the walls of the scala tympani. However, achieving an electrode geometry that has both a small cross section and the desired shape for mid-scalar placement can be challenging. As discussed above, the additional silicone layer that overcomes the resilience of the signal wires also thickens and stiffens the apical portion the electrode array.

The inventors have discovered that by forming flexural loops or arches in the wires between the electrodes, the straightening tendency of the signal wires can be minimized.

These flexural geometries may have a number of functions. The flexural geometries may reduce the overall stiffness of the wires and electrode array. Additionally or alternatively, the flexural geometries may create a spring force that tends to return the electrode array to a curved shape after straightening.

When the flexural geometries are included in the wire, the reduced stiffness and/or curling spring force of the wire may allow for the use of a one-step molding process to form the electrode array. In contrast to a two-step mold, a one-step mold may have a number of advantages. First, the handling and time associated with a one-step molding process can be less than with a two-step molding process. Consequently, a one step molded electrode arrays may be more cost effective than two-step molded electrode arrays. Additionally, the one-step molding process is adapted to produce an electrode array with a relatively small apical cross section. This relatively small apical portion is inserted into the deeper portions of the cochlea where the cochlear channels narrow. This may decrease contact between the electrode array and cochlear structures and require less insertion force during implantation.

FIG. 5A shows a top view of three apical electrodes (465) and the signal wires (455) that connect the electrodes (465) to the processor (185, FIG. 3). For purposes of illustration, the flexible body that covers the signal wires (455) and electrodes (465) has not been shown. In this implementation, the electrodes (465) are formed from shaped pieces of metal foil, that are then folded to capture the signal wires (455). As discussed above, each electrode (465) is electrically connected to one of the signal wires (455). In this example, the most apical electrode (465-1) is electrically connected to a first signal wire (455-1), the second electrode (465-2) is electrically connected to the second signal wire (455-2), and the third electrode (465-3) is electrically connected to the third signal wire (455-3). The electrodes (465) include wings (467) that fold over signal wires that pass to more apical electrodes. The wings (467) physically contain the wires (455) and form a wire bundle.

FIGS. 5B-5D show a variety of flexural geometries that can be formed in the wire between the electrodes. The term "flexural geometry" is used broadly to describe curved wire shapes between two electrodes. In some examples, the curved wire geometries may be formed between each of the electrodes in the electrode array. The flexural geometry may be any of a number of shapes, including but not limited to, an arch as shown in FIGS. 5B and 5C or a loop as shown in FIG. 5D.

The flexural geometry is formed in wire sections between electrodes and may reduce the bending stiffness of the wires and/or provide a spring force that returns the electrode array to its curled spiral shape. Because of the reduced bending stiffness and/or spring force produced by the flexural geometry in the wires, less silicone material is needed to hold the curvature of the apical portion of the electrode array. This results in a thinner curved electrode array. Because the additional silicone layer is not necessary, a single shot molding process can be used to produce the thinner, more flexible electrode array. This thinner, more flexible electrode array is suited for mid-scalar placement and reduces insertion trauma.

FIG. 5B is a cross sectional view taken along the line A-A. Electrodes (465-2, 465-3) are shown connected by a wire or bundle of wires (455). The wire (455) is formed into an arch between the electrodes (465), with each end of the arched wire (455) secured by an electrode (465). The arch is in a plane that is substantially parallel to the plane of curvature of the electrode array. The shape of the arch decreases the stiffness of the wires and provides a resilient spring force which allows the electrode array to conform more closely to its "as-so molded" shape. The arch may be formed prior to, during, or after placing the electrodes in the mold. The arch may have a variety of geometries. In this example, the arch has a first leg (490), a second leg (491), and a central curved portion (492). The radius of curvature of the central curved portion (492) may be adapted to the distance between the electrodes (465) or other design parameters.

FIG. 5C shows a flexural geometry that is made up of a substantially uniform arch (492) between the first electrode (465-2) and the second electrode (465-3). FIG. 5D shows flexural geometry that includes a looped wire (455) that intersects itself. In each of the examples given above, the plurality of wires that passes along the array of electrodes have a flexural geometry between each pair of adjacent electrodes and a substantially straight geometry over the electrodes and beneath the wings. The possibility of undesired short circuiting of the wires to the contact pads is reduced because the flexural geometry minimizes the tension in the wires. The substantially straight geometry of the wires as they pass over the electrodes allows the wings to fold over the wires and form a wire bundle. The examples given above are only illustrative examples of flexural geometries that reduce the overall bending stiffness of the wires and allow for straightening of the electrode without breaking wires or weld joints.

The wire flexural geometries may be formed in variety of ways. One method includes preforming the wire prior to connecting the wires to the electrodes. Another method includes forming the wire and electrode assembly and then manipulating the wires to form the desired flexural geometry. Other methods may include placing an object between the electrodes and under the wires, then forcing the wires over the object. In one example, the wires may be formed from small diameter wire, such as platinum/iridium wire with a diameter of 25 microns or less. For example, the wire is formed from an 80/20 platinum/iridium alloy and has a diameter of 20 microns. This relatively small diameter reduces the stiffness of the wire. In some examples, the flexural geometry may be partially formed during the assembly of the electrodes and wires. The flexural geometry is then further formed during the molding process. As described below, the wire/electrode assembly is wrapped around and inner wall of the mold. This plastically deforms the wires to create more pronounced curvature in the wires. The plastically deformed wires then have a memory or spring force which tends to curl the electrode back toward the molded shape after straightening.

FIG. 6A shows a single shot mold (600) for a mid-scalar electrode array with a reduced apical thickness. The electrodes (465) and connecting arched wires (455) are placed in the mold (600). The arched wires (455) readily conform to the shape of the mold (600) and have a reduced bending stiffness compared to similar wires with a straight geometry. Further, when wrapped around the inner curve of the mold, the wires are overbent. This puts some 'spring' tension in the flexural geometry between each and every electrode that holds the curvature and resists the straightening of the electrode.

The combination of reduced bending stiffness and bending of the wires into tight radius in the mold reduces the tendency of the electrode array to undesirably increase in the radius of curvature after molding or after straightening. Consequently, less silicone is need at the apical end of the electrode array to hold the curved shape and thickness of the apical portion can be reduced. This allows the molded shape of the electrode array to be formed in a single mold at the desired radius of curvature without self interference by the electrode array. As discussed above, the silicone is injected into the mold cavity (605) to encapsulate the wires (455, 465) and electrodes. The contact surface of the electrodes (465) is not covered with the silicone. After curing, the electrode array is removed from the mold (600).

FIG. 6B shows the completed cochlear lead (190) which has been removed from the mold. When the cochlear lead (190) is removed from constraints of the mold, the cochlear lead tends to relax and uncurl. This uncurling tendency is driven primarily by the silicone. Because the wires and the flexural geometries in the wires have been formed around the tighter radius of curvature of the mold, the wires tend to generate a spring force which resists the uncurling motion. This produces an electrode array which has a thin apical cross section and a mid-scalar geometry for insertion to 360 degrees or more into the cochlea. The insertion depths of the electrode array are shown in FIG. 6B for purposes of illustration. According to one illustrative example, the insertion depth or curvature of the electrode array in degrees is determined by drawing a line from the cochleostomy marker (610) to the center (615) of the curvature. The intersection between the line and the electrode array indicates an insertion depth of 360°. When inserted into the cochlea to the full depth, the tip of this illustrative cochlear lead (190) is designed to extend into the cochlear duct significantly more than 360°. Other cochlear lead designs may be inserted deeper or shallower than the illustrated cochlear lead (190). In the relaxed geometry shown in FIG. 6B, the cochlear lead has a shape that corresponds to a mid-scalar position in a cochlear duct.

The cochlear lead has a decreasing cross sectional area from the basal end of the electrode array to the apical end of the electrode array. A first cross section C-C is taken through a basal electrode and a second reduced cross sectional area B-B is taken through an apical electrode. In one embodiment, the first cross section has an area of approximately 0.40 mm$^2$ and the reduced cross section area has an area of approximately 0.23 mm$^2$. Thus, for this precurved electrode array with a lumen, the reduced cross sectional area is approximately 50 percent smaller than the first cross sectional area.

Additionally or alternatively, the reduction in cross-sectional area can be described as the ratio between the overall cross sectional area and wire is cross sectional area at a given region of the electrode array. At the basal electrode, the cross sectional area of the array body is 0.40 mm$^2$ and the cross sectional area of the 17 wires is approximately 0.021 mm$^2$. Thus, the ratio of the total cross sectional area to the cross sectional area of the wires at the most basal electrode is approximately 19.

At the most apical electrode, the cross sectional area of the array body is 0.23 mm$^2$ and the cross section of two 20 micron diameter wires is approximately 0.0025 mm$^2$. Thus, at the most apical electrode, the ratio of the cross sectional area of the array body to the cross sectional area of the wires at the most apical electrode is approximately 92. In other illustrative implementations, the ratio of cross sectional area of the array body to the cross sectional area of the wires at the most apical electrode is less than 120.

Figure 6C:
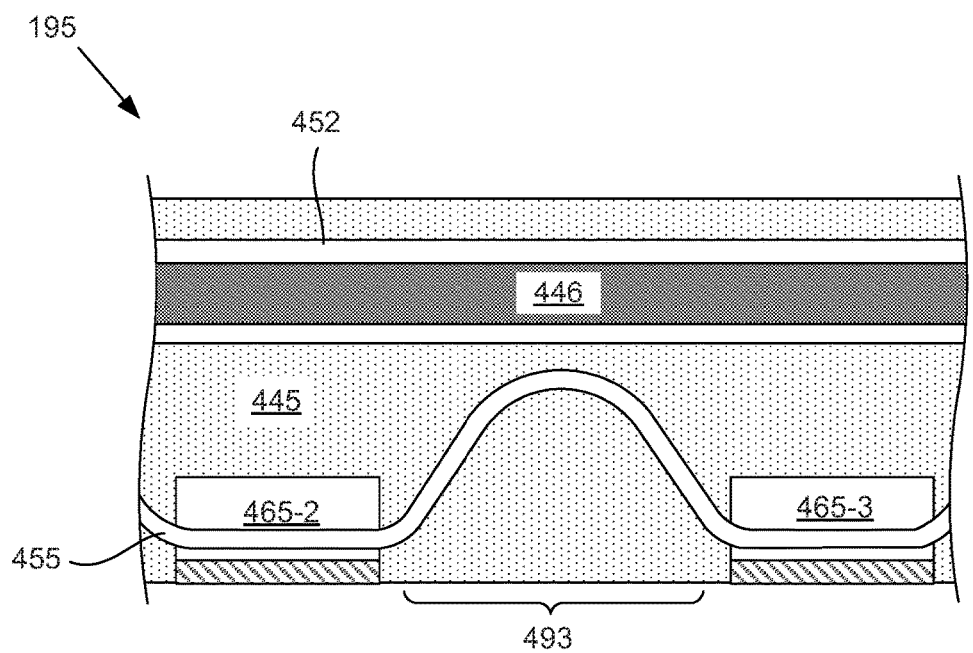
FIGS. 6C-6D are cross sectional diagrams of a portion of an illustrative mid-scalar electrode, according to one example of principles described herein.

FIG. 6C is a cross sectional diagram of a portion of the electrode array (195). A stiffener (446) has been inserted through a lumen (452) in the flexible body (445). This straightens the electrode array (195) and flattens the arch (493).

Figure 6D:
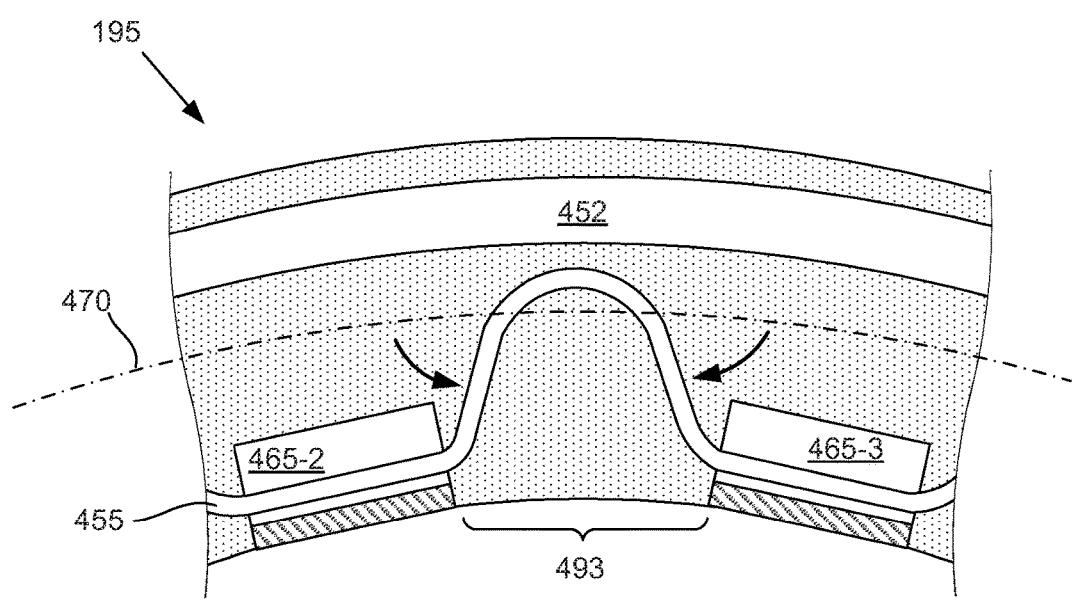

FIG. 6D shows the stiffening element removed from the lumen (446) and contraction of the arch (493) shown by two curved arrows. The contraction of the arch may be due to both the spring force of the wire and compression of the silicone around the wire. Similar contraction occurs in the arches between each of the other electrodes. This curls the electrode array (195) into its relaxed shape and the shape of the cochlea. In one implementation, at least a portion of the arch (493) or other flexural geometry extends past the neutral bending axis (470) of electrode array (195). The neutral bending axis (493) passes through the electrode array (195) along a plane in which there are no longitudinal stresses or strains during bending. A variety of factors may influence where the neutral bending axis occurs, including, the stiffness of the various components within the electrode array (195), the amount of curvature in the electrode array (195), and the cross sectional geometry of the electrode array (195). Extending the flexural geometry to the neutral bending axis minimizes the stresses in the wire when straightening the electrode.

The wire configurations given above are illustrative examples geometries which could reduce the stiffness of the electrode array and/or provide a spring force which tends to tighten the curl of the electrode array. For example, if an annealed wire with a small diameter and pliable characteristics is selected, the flexural geometries may serve primarily to further reduce the stiffness of the wire. The annealed/soft wire may not significantly contribute a spring force which tends to tighten the curl of the electrode array. If, on the other hand, a relatively stiffer and/or larger wire was used, the bending stiffness of the electrode array may not substantially decrease, but the wire may exert a substantial amount of spring force on the electrode array that tends to curl it into the desired spiral shape. Either of these approaches could be used to create a mid-scalar electrode array with a reduce cross section apical portion that is designed to be inserted at least 360° into the cochlea. Additionally, these two approaches could be combined by selecting a wire with an intermediate diameter and/or stiffness. The flexural geometries in the wire could then simultaneously reduce the stiffness of the electrode array and produce a spring force that tends to resist the straightening of the electrode array.

Figure 7:
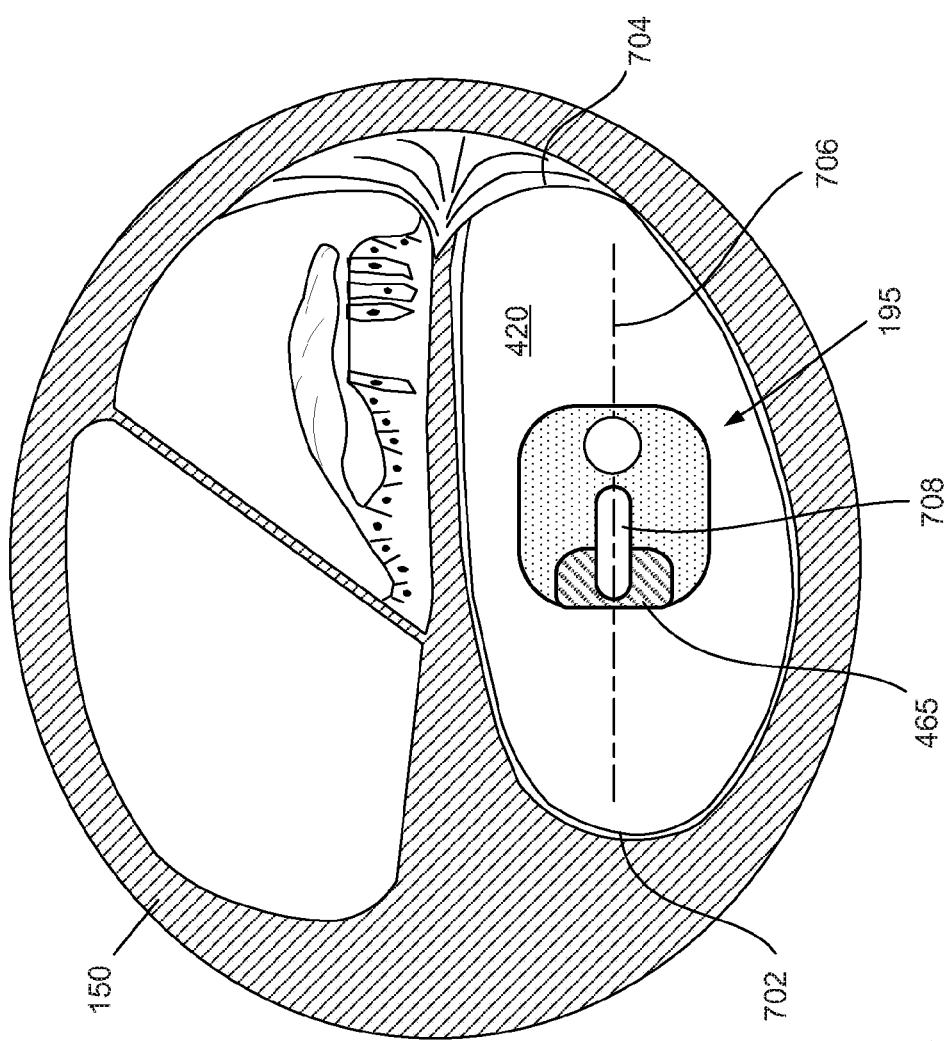
FIG. 7 is a cross sectional view of an illustrative mid-scalar electrode inserted into a cochlear duct, according to one example of principles described herein.

FIG. 7 is a cross sectional view of a portion of a cochlea (150) that shows an illustrative electrode array (195) in a mid-scalar position. Ideally the curvature of the electrode array (195) matches the curvature of the ducts in the cochlea (150) and maintains the mid-scalar placement along the length of the electrode array. The electrode array (195) includes electrodes (465) and a flexural wire geometry (708) between each of the electrodes. In this implementation, the plane (706) of the wire geometry (708) intersects both the lateral wall (704) and the medial wall (702). An alternative method for measuring the orientation of the flexural geometries is to measure the plane (706) of the wire geometry with respect to the exposed surface of the electrodes (465). For example, flexural geometry may be oriented in a plane (706) that is perpendicular to exposed surfaces of the adjacent electrodes (465). The plane (708) of the wire geometry is defined as a plane that passes through the center line of the wire or wire bundle.

Figure 8:
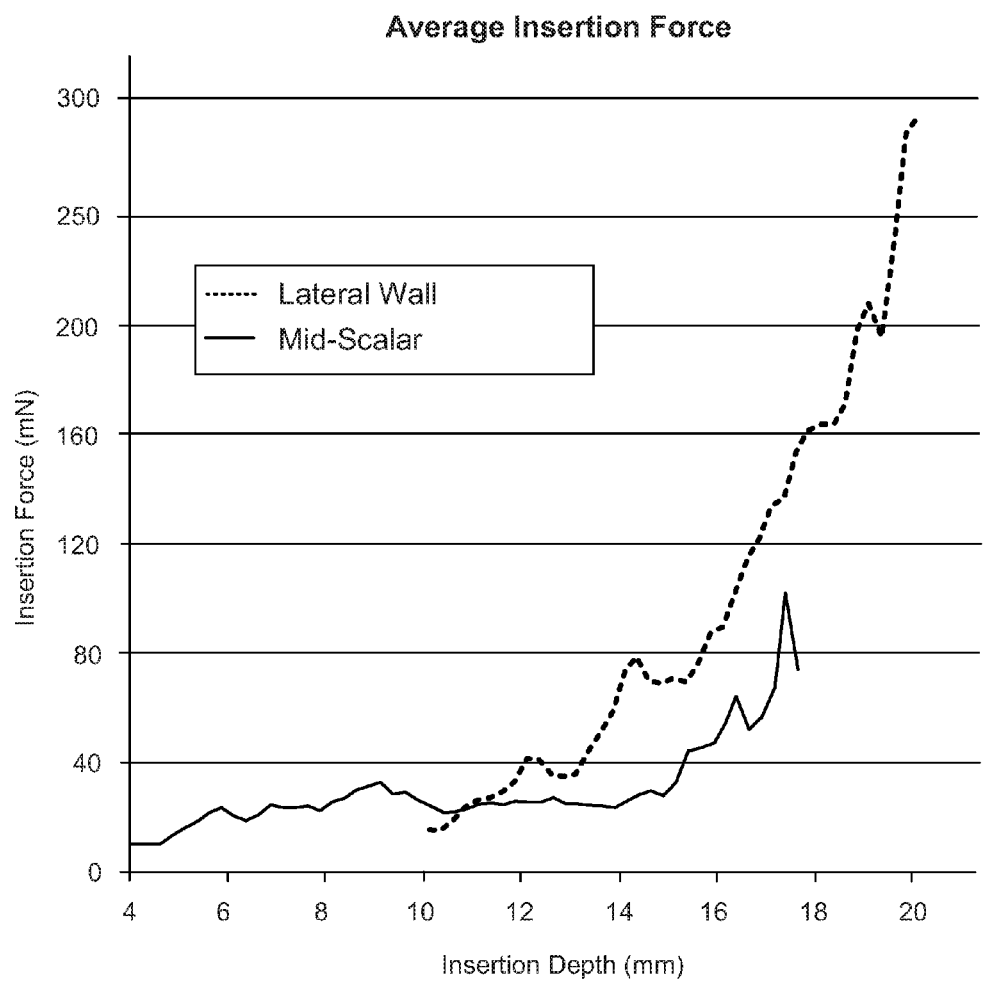
FIG. 8 is a graph that compares average insertion forces for lateral wall cochlear leads and mid-scalar cochlear leads, according to one example of principles described herein.

FIG. 8 is a graph that compares average insertion forces for lateral wall cochlear leads and mid-scalar cochlear leads. The horizontal axis shows insertion depth in millimeters and vertical axis shows insertion force in millinewtons. The force measurements were made using a three axis force measurement system during the insertion of cochlear leads into fixed human temporal bones without lubricating agents other than saline. The lateral wall data is shown as a dotted line that represents the average insertion force of 12 lateral wall cochlear leads. The solid line represents the average insertion force of 9 mid-scalar cochlear leads. The lateral wall forces rise exponentially with insertion depth. For example, at an insertion depth of 14 millimeters, the average insertion force for a lateral wall cochlear lead was about 80 millinewtons. At an insertion depth of 18 millimeters, the insertion force is approximately 160 millinewtons, and at a depth of 20 millimeters, the insertion force was approximately 290 millinewtons. In contrast, the mid-scalar designs were inserted with consistently lower forces than the lateral wall designs. The highest peak on the mid-scalar data occurs at an insertion depth of approximately 17 millimeters. This peak is due to stylet extraction from the lumen in the mid-scalar cochlear leads. The peak can be reduced by using an insertion tool with an automated stylet retraction mechanism. The lower insertion forces indicate that the illustrative mid-scalar designs cause less trauma to the cochlear tissues.

Figure 9:
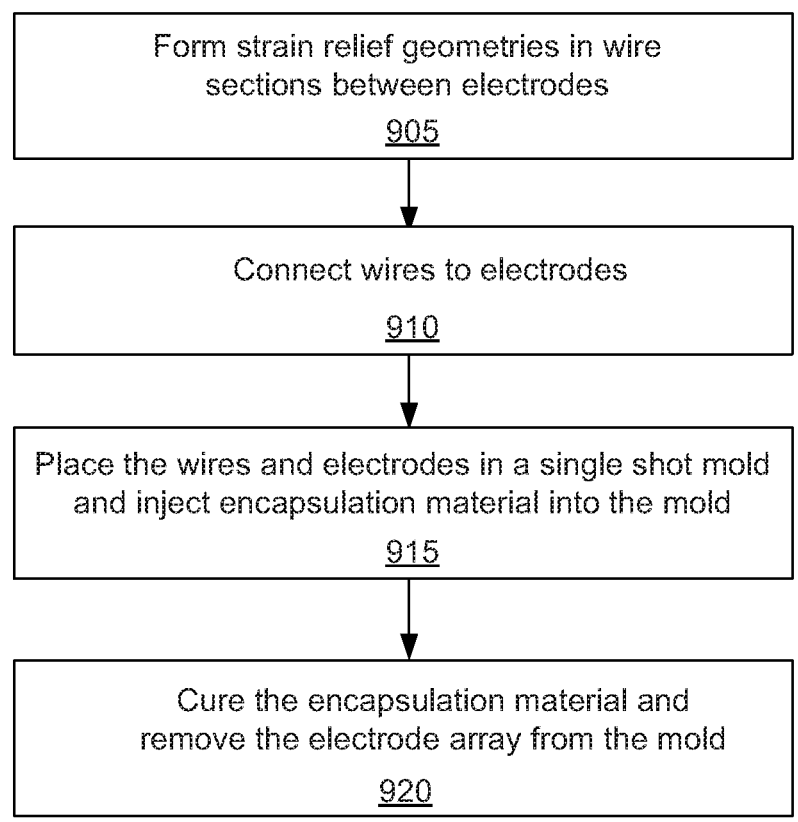
FIG. 9 is a method for forming a mid-scalar electrode, according to one example of principles described herein.

FIG. 9 is a method (900) for forming an illustrative mid-scalar electrode array using a single step molding process which produces a completed silicone body. Flexural geometries are formed in wire sections which will be located between electrodes (block 905). The wires may be formed from a variety of materials, including platinum and platinum/iridium alloys. For example, the wires may be formed from a platinum iridium alloy and have a diameter of less than 25 microns. The wire may be selected so that it retains the flexural geometry in portions of the wire located between the electrodes through multiple bending cycles. The flexural geometry may be oriented in a plane which intersects both the medial and laterals walls of the scala tympani.

The wires are individually paired and connected to the electrodes (block 910). For example, the wires may be welded or soldered to the individual electrodes. The wires that pass over the electrodes to more apical positions are enclosed by the wings of the electrodes. This technique is described in U.S. patent application Ser. No. 12/781,137, now U.S. Pat. No. 8,880,193, entitled "Cochlear Electrode Array" to Timothy Beerling et al., filed on May 17, 2010, which is hereby incorporated by reference in its entirety. The wires and electrodes are placed in a single shot mold and encapsulating material is injected into the mold (block 915). For example, liquid injection of silicone can be used to encapsulate the wires and electrodes. The encapsulating material is cured and the electrode array is removed from the mold (block 920). The flexural geometries in portions of the wire located between the electrodes may be formed such that the flexural geometry extends into the silicone body at least to the neutral bending axis of the electrode array. This minimizes the stress in the portion of the wire near the neutral axis when straightening or bending the electrode.

The steps described above are only illustrative examples. The steps in the method may be combined, eliminated, reordered, or additional steps may be added. The order in which the steps are presented is not limiting. For example, the steps of connecting the wires to the electrodes and forming flexural geometries in the wires can be performed simultaneously or in reverse order. Examples of additional steps that may be added to the method include cleaning and testing steps.

In sum, flexural geometries in wires between electrodes in a cochlear electrode array reduce the tendency of the electrode array to uncoil/open after molding. This reduces the amount of encapsulation material on the apical portion of the electrode array and allows the electrode array to be produced using a single shot mold. The thinner electrode array can be more easily inserted into a mid-scalar position with reduced trauma to the cochlea.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A cochlear lead, the cochlear lead comprising:
a flexible body;
an array of electrodes in the flexible body; and
a plurality of wires passing along the array of electrodes, wherein the plurality of wires comprise a plurality of flexural elements with a single flexural element between each pair of adjacent electrodes, each flexural element consisting of a loop, an arch, or a semicircle formed in the wire, wherein the flexural elements are configured to create a spring force that tends to return the flexible body to a mid-scalar geometry after straightening, and wherein the spring force is partially based on resisting stiffness or curling of the plurality of wires.

2. The lead of claim 1, wherein the plurality of flexural elements is oriented to reduce a stiffness of the wires in a plane orthogonal to an exposed surface of an adjacent electrode.

3. The lead of claim 1, wherein the electrodes of the array have uniform thickness.

4. The lead of claim 1, wherein the plurality of flexural elements contain only curvatures.

5. The lead of claim 1, wherein the plurality of the flexural elements reduce a prevalence of shorts in the lead.

6. The lead of claim 1, wherein the flexural element is in a plane substantially parallel to a plane of curvature of the electrode array.

7. A cochlear lead, the cochlear lead comprising:
a flexible body;
an array of electrodes in the flexible body;
a wire between each electrode and the proximal end of the flexible body, wherein each wire is oriented in a straight line along a length of the lead over each electrode and each wire has a flexural element between each pair of electrodes such that the wire over the electrode is static relative to the electrode and the wire between the electrodes flexes at the flexural element to accommodate bending of the flexible body and creates a spring force that tends to return the flexible body to a mid-scalar geometry after straightening, and wherein the spring force is partially based on resisting stiffness or curling of the plurality of wires.

8. The lead of claim 7, wherein each flexural element is an arch.

9. The lead of claim 7, wherein each flexural element is a semicircle.

10. The lead of claim 7, wherein the flexural element located in the wire between the pair of electrodes reduces a rate of shorts.

11. The lead of claim 7, wherein each flexural element extends beyond a neutral bending axis of the flexible body.

12. The lead of claim 7, further comprising a lumen in the flexible body, wherein a plane in which an entire flexural element lies intersects the lumen.

13. The lead of claim 7, further comprising a lumen in the flexible body and a stiffening element in the lumen, wherein a flexural element opposes straightening of the flexible body by the stiffening element.

14. The lead of claim 7, wherein an electrode comprises a wing folded parallel to an exposed surface of the same electrode.

15. The lead of claim 7, wherein a ratio at a most distal electrode of a cross sectional area of the flexible body to a cross sectional area of the wires is between 90 and 120.

16. The lead of claim 7 wherein the wire between each electrode and the proximal end of the flexible body electrically connects each electrode to a processor.

17. A method of forming a cochlear lead with a reduced apical cross section, the method comprising:
connecting a wire to a first electrode;
forming in the connected wire, a single arch having a radius of curvature between the first electrode and a second electrode adjacent to the first electrode, the wire passing straight over the surface of the second electrode such that the wire occupies a minimum area over the second electrode, wherein the single arch is configured to create a spring force; and
overmolding the wire and electrodes with encapsulation material in a single molding operation to form a completed silicone body, wherein the spring force is partially based on an amount of silicone in the completed silicone body and wherein the spring force tends to return the silicone body to a mid-scalar geometry after straightening.

18. The method of claim 17, wherein a plane comprising all of the arch is perpendicular to an exposed surface of the first electrode.

19. The method of claim 17, further comprising folding a wing on the first or second electrode such that a surface of the wing is parallel to an exposed surface of the first or second electrode.

* * * * *